(12) United States Patent
Keller et al.

(10) Patent No.: US 8,486,664 B2
(45) Date of Patent: Jul. 16, 2013

(54) ENZYMATIC PRODUCTION OF AN ETHYLENICALLY UNSATURATED GLYCOSIDE USING POLYSACCHARIDES

(75) Inventors: Harald Keller, Ludwigshafen (DE); Katja Loos, Groningen (NL); Wouter Kloosterman, Groningen (NL)

(73) Assignee: BASF SE, Ludwigshafen (DE)

( * ) Notice: Subject to any disclaimer, the term of this patent is extended or adjusted under 35 U.S.C. 154(b) by 173 days.

(21) Appl. No.: 13/192,761

(22) Filed: Jul. 28, 2011

(65) Prior Publication Data

US 2012/0028307 A1 Feb. 2, 2012

Related U.S. Application Data

(60) Provisional application No. 61/368,728, filed on Jul. 29, 2010.

(51) Int. Cl.
*C12P 19/60* (2006.01)

(52) U.S. Cl.
USPC .............. 435/74; 435/200; 435/201; 435/209

(58) Field of Classification Search
USPC .................................. 435/74, 200, 201, 209
See application file for complete search history.

(56) References Cited

U.S. PATENT DOCUMENTS

| 3,878,191 A | 4/1975 | Fukumoto et al. |
|---|---|---|
| 2011/0313097 A1 | 12/2011 | Keller et al. |
| 2012/0016114 A1 | 1/2012 | Keller et al. |

FOREIGN PATENT DOCUMENTS

| EP | 0 394 496 A1 | 10/1990 |
|---|---|---|
| JP | 09003089 | 1/1997 |

OTHER PUBLICATIONS

Li et al. Bioorganic and Medicinal Chemistry (1999) 7: 1549-1558.*
U.S. Appl. No. 13/192,771, filed Jul. 28, 2011, Keller, et al.
U.S. Appl. No. 13/264,634, filed Dec. 29, 2011, Keller, et al.
Shuichi Matsumura, et al., "Enzymatic synthesis of novel vinyl monomers bearing β-D-galactopyranoside residue", Makromol. Chem., Rapid Commun., vol. 14, 1993, pp. 55-58.
Iqbal Gill, et al., "Enzymatic Glycosylation in Plasticized Glass Phases: A Novel and Efficient Route to O-Glycosides", Angew. Chem. Int. Ed., vol. 39, No. 21, 2000, pp. 3804-3808.
James Lalonde, et al., "Immobilization of Enzymes", Wiley-VCH, Enzyme Catalysis in Organic Synthesis, vol. 1, 2002, pp. 163-184.
F. van Rantwijk, et al., "Glycosidase-catalysed synthesis of alkyl glycosides", Journal of Molecular Catalysis B: Enzymatic, vol. 6, 1999, pp. 511-532.
International Search Report mailed Oct. 12, 2011 issued in PCT/EP2011/062780 filed on Jul. 26, 2011.
Database EPODOC European Patent Office—XP-002659706, Jan. 7, 1997.

* cited by examiner

*Primary Examiner* — Susan Hanley
(74) *Attorney, Agent, or Firm* — Oblon, Spivak, McClelland, Maier & Neustadt, L.L.P.

(57) ABSTRACT

Ethylenically unsaturated glycosides of formula I

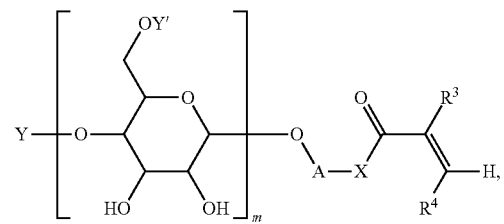

wherein Y, Y', m, A, X, $R^3$ and $R^4$ have the meanings given in the description, are produced by reacting an ethylenically unsaturated compound of formula II

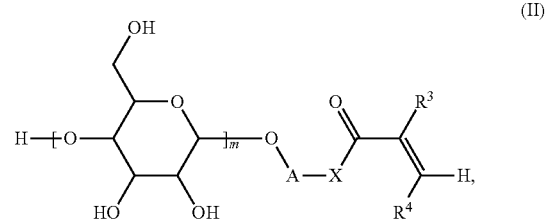

with a polysaccharide comprising 10 or more monosaccharide units, such as starch, amylose, amylopectin, cellulose, in the presence of a glycosidase, such as an amylase, cellulase, glucosidase or and galactosidase, or a glycosyltransferase, such a cyclomaltodextrin glucanotransferase.

8 Claims, No Drawings

ENZYMATIC PRODUCTION OF AN ETHYLENICALLY UNSATURATED GLYCOSIDE USING POLYSACCHARIDES

The invention relates to a method for producing an ethylenically unsaturated glycoside by reacting an ethylenically unsaturated compound with a polysaccharide in the presence of a glycosidase or a glycosyltransferase.

Polymers comprising sugar residues (saccharide copolymers) may share typical properties of saccharides such as good water solubility, high electrolyte stability, colloidal stability in hot water, strong interaction with surfaces such as cotton and non-toxicity. These specific properties open a variety of applications for such polymers. It is therefore of great interest to develop cost-effective methods for producing well-defined saccharide copolymers and their respective monomers. Such monomers may be polymerizable ethylenically unsaturated glycosides which result by glycosidic coupling a saccharide and an ethylenically unsaturated alcohol. The synthesis of such glycosides involves a number of challenges. There are many possibilities for the formation of positional isomers in which different hydroxyl groups of the saccharide become involved in bond formation. Further, there is the potential for the formation of different anomeric forms. Chemical synthesis of most monomers bearing sugar residues is therefore generally not feasible and results in poor yields of the desired monomer.

The application of enzymes has been considered an alternative approach for producing glycosidic monomers. In contrast to chemical synthesis, enzyme-catalyzed reactions of unprotected sugars usually yield a much more structurally homogeneous product due to their high stereoselectivity.

In general there are two approaches used for enzymatic synthesis of glycosides: thermodynamically controlled reverse hydrolysis and kinetically controlled transglycosylation. Approaches to use glycosidases, which catalyze glycoside hydrolysis in vivo, for glycoside synthesis by reverse hydrolysis are described, for example, by I. Gill and R. Valivety (Angew. Chem. Int. Ed. 39(21):3804-3808, 2000). Transfer of glycosyl units to non-sugar compounds with primary hydroxyl groups by enzymatically catalyzed transglycosylation has been shown, for example, by S. Matsumura et al. (Makromol. Chem., Rapid Commun. 14:55-58, 1993).

Polysaccharides such as cellulose or starch are inexpensive and readily available. It was therefore an object of the present invention to develop a method for the production of ethylenically unsaturated glycosides using polysaccharides as source of glycosyl units.

Thus, the present invention provides a method for producing an ethylenically unsaturated glycoside of formula I

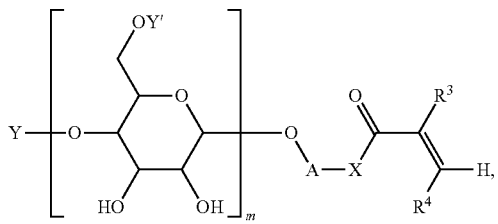

(I)

wherein
Y and Y' are independently H, or a monosaccharide or a linear or branched oligosaccharide comprising from 2 to 12 monosaccharide units, wherein at least one of Y and Y' is other than H;

m is an integer of from 0 to 3;
A is $C_{2-20}$ alkylene or $-R^6-O-[-R^6-O-]_x-C_{2-20}$ alkylene;
X is selected from the group consisting of $-O-$, $-NH-$ and $-NR^5-$,
$R^3$ is selected from the group consisting of $-H$, and $C_{1-10}$ alkyl;
$R^4$ is selected from the group consisting of $-H$, $-COOH$ and $-COO^- M^+$;
$R^5$ is $C_{1-10}$ alkyl;
$R^6$ is $-C_2H_4-$ or $-C_3H_6-$;
$M^+$ is selected from the group consisting of $Li^+$, $Na^+$, $K^+$ and $NH_4^+$; and
x is an integer of from 0 to 200;
comprising reacting an ethylenically unsaturated compound of formula II

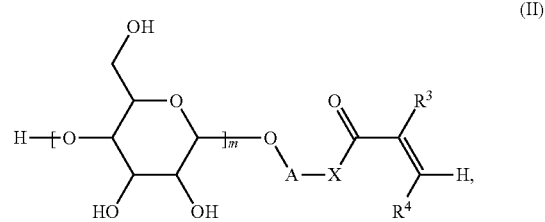

(II)

with a polysaccharide of comprising 10 or more monosaccharide units
in the presence of a glycosidase or a glycosyltransferase.

In preferred embodiments, Y' is H and Y is a monosaccharide, or a linear or branched oligosaccharide comprising from 2 to 12 monosaccharide units.

In preferred embodiments, Y is

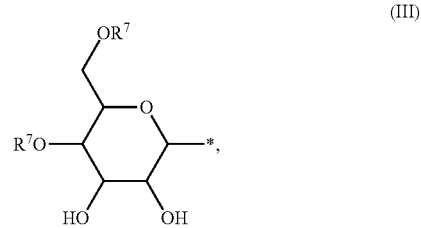

(III)

wherein $R^7$ is $-H$ or a radical of formula IV:

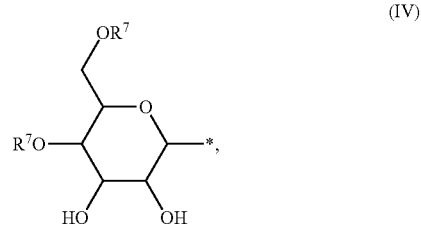

(IV)

wherein in peripheral monosaccharide units $R^7$ is H.

DEFINITIONS

The term "monosaccharide" as used herein refers to a single unit of a polyhydroxyaldehyde forming an intramolecular hemiacetal the structure of which including a sixmembered ring of five carbon atoms and one oxygen atom. Monosaccharides may be present in different diasteromeric forms, such as α or β anomers, and D or L isomers. An "oligosaccharide" consists of short chains of covalently linked monosaccharide units. Oligosaccharides comprise disaccharides which include two monosaccharide units as well as trisaccharides which include three monosaccharide units. A "polysaccharide" consists of long chains of covalently linked monosaccharide units.

The term "glycosidic bond" or "glycosidic linkage" is a type of chemical bond or linkage formed between the anomeric hydroxyl group of a saccharide or saccharide derivative (glycone) and the hydroxyl group of another saccharide or a non-saccharide organic compound (aglycone) such as an alcohol. The reducing end of the di- or polysaccharide lies towards the last anomeric carbon of the structure, and the terminal end is in the opposite direction.

An "enzymatically catalyzed" or "biocatalytic" method as used herein means that said method is performed under the catalytic action of an enzyme, in particular of a glycosidase or a glycosyltransferase. The method can be performed in the presence of said glycosidase or glycosyltransferase in isolated (purified, enriched) or crude form.

The term "glycosidase" also includes variants, mutants and enzymatically active portions of glycosidases.

Likewise, the term "glycosyltransferase" also includes variants, mutants and enzymatically active portions of glycosyltransferases.

Catalytic amounts of enzyme are expressed in "U" ("Unit" or "unit"), wherein 1 U equals the amount of enzyme which catalyses the reaction of 1 μmol substrate per minute under specific conditions (usually 37° C. and pH 7.5). Thus, for example, 10 U glycosidase equals a catalytic amount of enzyme required for the reaction of 10 μmol saccharide substrate per minute. Catalytic amounts of maltogenic amylase can be expressed in "MANU" (Maltogenic Amylase Novo Unit), wherein 1 MANU equals the catalytic amount of enzyme required for the reaction of 1 μmol maltotriose per minute under standard conditions (10 mg/ml maltotriose, 37° C., pH 5.0, reaction time of 30 min). The catalytic amount of an enzyme can be determined by methods well know in the art.

The term "alkyl" comprises $C_{1-10}$ alkyl radicals which are linear or branched radicals having from 1 to 10 carbon atoms. Examples thereof are methyl, ethyl, n-propyl, isopropyl, n-butyl, 2-butyl, isobutyl or tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, nonyl, and decyl, as well as their constitutional isomers such as 2-ethylhexyl.

The term "alkylene" comprises $C_{2-20}$ alkylene diradicals which are linear or branched diradicals having from 1 to 20 carbon atoms.

The term "ethylenically unsaturated" refers to a compound comprising a non-aromatic C=C double bond. Specifically an "ethylenically unsaturated glycoside" as used herein refers to a glycoside consisting of a saccharide that is glycosidically linked to an ethyllenically unsaturated alcohol.

In the method of the present invention, the polysaccharide acts as a source of saccharide units that are transferred to the ethylenically unsaturated compound of formula II to form the ethylenically unsaturated glycoside of formula I. The transferred saccharide units are monosaccharide units such as glucose, galactose, or mannose units; disaccharide units such as maltose, lactose or cellobiose units; trisaccharide units such as maltotriose units; or other oligosaccharide units such as maltohexaose, or a mixture thereof. For example, the transferred saccharide units are D-glucose, maltose, cellobiose, maltotriose, or maltohexaose units. The transferred oligosaccharide units can be linear or branched.

The polysaccharide used in the method of the present invention comprises 10 or more monosaccharide units. Typically, the number of monosaccharide units of the polysaccharide is from about 300 to about 200,000, for example from about 2,000 to about 200,000; from about 300 to about 3,000; or from about 300 to about 10,000. The size of polysaccharides, i.e. the number of monomer units, may be decreased by pre-processing, e.g. using acid and/or heat or enzymes such as α-amylases. The polysaccharides may be linear chains of monosaccharide units linked by (1→4)-glycosidic bonds; or may be branched by the formation of (1→6)-glycosidic bonds, e.g. every 24 to 30 monomer units. The terminal monosaccharide units of the saccharide chain (and side chains) are herein also called peripheral monosaccharide units.

In particular, the polysaccharide may be a compound of formula V

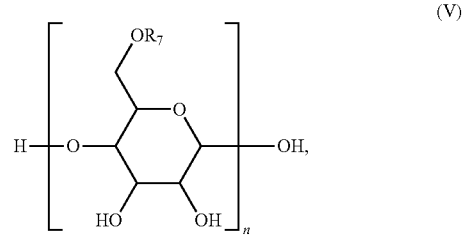

wherein $R^7$ is —H or a radical of formula VI:

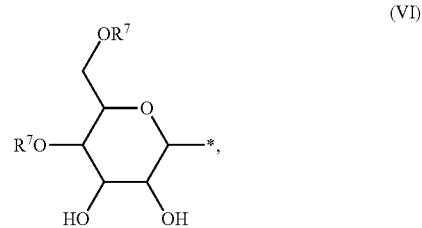

wherein in peripheral monosaccharide units $R^7$ is H and n is such that the number of monosaccharide units encompassed by the recurring units in brackets is 10 or more, e.g., from about 300 to about 200,000.

Exemplary polysaccharides comprise starch, amylose, amylopectin, cellulose, and mixtures thereof.

In one embodiment, m is 0, i.e. the ethylenically unsaturated compound of formula II is an ethylenically unsaturated alcohol selected from hydroxyalkyl (meth)acrylates, N-hydroxyalkyl (meth)acrylamides, mono(hydroxyalkyl) esters of maleic acid, and salts thereof; or an ethoxylated, propoxylated or ethoxylated and propoxylated derivative thereof.

In other embodiments, m is 1, 2 or 3, i.e. the ethylenically unsaturated compound of formula II is an ethylenically unsaturated mono-, di- or triglycoside consisting of a mono-, di- or trisaccharide component and an alcohol component selected from the above ethylenically unsaturated alcohols.

Preferred ethylenically unsaturated alcohols of formula II are selected from 2-hydroxyethyl acrylate, 2-hydroxyethyl methacrylate, 3-hydroxypropyl acrylate, 3-hydroxypropyl methacrylate, N-(2-hydroxyethyl)acrylamide, N-(2-hydroxyethyl)methacrylamide, N-(3-hydroxypropyl)acrylamide, N-(3-hydroxypropyl methacrylamide, (2-hydroxyethyl)hydrogen maleate, and glycosides thereof.

In certain embodiments, A is $C_{2-6}$ alkylene, X is —O—, and $R^3$ is —H or —CH$_3$.

In further embodiments, m is 1, Y' is H and Y is a monosaccharide or a linear or branched oligosaccharide comprising from 2 to 12 monosaccharide units, and preferably is a monosaccharide, a disaccharide or a trisaccharide.

In the method of the present invention, the reaction of polysaccharide and ethylenically unsaturated alcohol or glycoside is catalyzed by an enzyme selected from a glycosidase and a glycosyltransferase. Typically, enzymes show a high specificity regarding to the reactions they catalyze, the substrates that are involved in these reactions.

Glycosidases, a type of enzyme also known as glycoside hydrolases, are enzymes capable of catalyzing the hydrolysis of O- and S-glycosidic compounds. Further, glycosidases can be used for catalyzing the formation of glycosidic bonds through reverse hydrolysis, where the reaction equilibrium position is reversed, or transglycosylation, where a glycoside moiety is transferred from one glycoside, i.e. the donor glycoside, to another glycoside, i.e. the acceptor glycoside, to form a new glycoside. Glycosidases are assigned with enzyme classification number EC 3.2.1.x.

Glycosyltransferase are enzymes capable of catalyzing transglycosylation, a reaction wherein a glycoside moiety is transferred from one glycoside, i.e. the donor glycoside, to another glycoside, i.e. the acceptor glycoside, to form a new glycoside. Glycosyltransferases comprise hexosyltransferases which catalyze a transglycosylation wherein the transferred glycoside moiety is a hexose. Hexosyltransferases are assigned with enzyme classification number EC 2.4.1.x.

The enzyme may be used in a purified form, as an enriched concentrate or as a crude enzyme preparation.

Suitably, the glycosidase present in the method of the invention is selected from the group consisting of amylases, cellulases, glucosidases and galactosidases.

α-Amylase is an enzyme having enzyme classification number EC 3.2.1.1, and is also known as glycogenase, endoamylase, Taka-amylase A, or 1,4-α-D-glucan glucanohydrolase. α-Amylases are capable of catalyzing the endohydrolysis of (1→4)-α-D-glucosidic linkages in polysaccharides containing three or more (1→4)-α-linked D-glucose units, such as starch and glycogen, thereby releasing reducing groups in the α-configuration.

β-Amylase is an enzyme assigned with enzyme classification number EC 3.2.1.2, and is also known as saccharogen amylase, glycogenase, or 1,4-α-D-glucan maltohydrolase. β-Amylases are capable of catalyzing the hydrolysis of (1→4)-α-D-glucosidic linkages in polysaccharides, such as starch and glycogen thereby releasing successive β-maltose units from the non-reducing ends of the polysaccharide chains.

Cellulase is an enzyme assigned with enzyme classification number EC 3.2.1.4, and is also known as endo-1,4-β-D-glucanase, β-1,4-glucanase, β-1,4-endoglucan hydrolase, celluase A, cellulosin AP, endoglucanase D, alkali cellulase, cellulase A 3, celludextrinase, 9.5 cellulase, avicelase, pancellase SS, or 1,4-(1,3;1,4)-β-D-glucan 4-glucanohydrolase. Cellulases are capable of catalyzing the endohydrolysis of (1→4)-β-D-glucosidic linkages in cellulose, lichenin and cereal β-D-glucans as well as 1,4-linkages in β-D-glucans also containing 1,3-linkages.

α-Glucosidase is an enzyme assigned with enzyme classification number EC 3.2.1.20, and is also known as maltase, glucoinvertase, glucosidosucrase, maltaseglucoamylase, α-glucopyranosidase, glucosidoinvertase, α-D-glucosidase, α-glucoside hydrolase, or α-1,4-glucosidase. α-Glucosidases are capable of catalyzing the hydrolysis of terminal, non-reducing (1→4)-linked α-D-glucose residues thereby releasing α-D-glucose.

β-Glucosidase is an enzyme assigned with enzyme classification number EC 3.2.1.21, and is also known as gentiobiase, cellobiase, emulsin, elaterase, aryl-β-glucosidase, β-D-glucosidase, β-glucoside glucohydrolase, arbutinase, amygdalinase, p-nitrophenyl (β-glucosidase, primeverosidase, amygdalase, limarase, salicilinase, or β-1,6-glucosidase. β-Glucosidases are capable of catalyzing the hydrolysis of terminal, non-reducing β-D-glucosyl residues thereby releasing β-D-glucose.

α-Galactosidase is an enzyme assigned with enzyme classification number EC 3.2.1.22, and is also known as melibiase, α-D-galactosidase, α-galactosidase A, or α-galactoside galactohydrolase. α-Galactosidases are capable of catalyzing the hydrolysis of terminal, non-reducing α-D-galactose residues in α-D-galactosides, including galactose oligosaccharides, and galactomannans.

β-Galactosidase is an enzyme assigned with enzyme classification number EC 3.2.1.23, and is also known as lactase, β-lactosidase, maxilact, hydrolact, β-D-lactosidase, S 2107, lactozym, trilactase, β-D-galactanase, oryzatym, or sumiklat. β-Galactosidases are capable of catalyzing the hydrolysis of terminal non-reducing β-D-galactose residues in β-D-galactosides.

The glycosyltransferase present in the method of the invention may be a glycosyltransferase such as a hexosyltransferase, for example cyclomaltodextrin glucanotransferase or dextransucrase.

Cyclomaltodextrin glucanotransferase is an enzyme assigned with enzyme classification number EC 2.4.1.19, and is also known as *Bacillus macerans* amylase, cyclodextrin glucanotransferase, cyclodextrin glycosyltransferase, cyclomaltodextrin glucotransferase, cyclomaltodextrin glycosyltransferase, konchizaimu, cyclizing α-1,4-glucan 4-glycosyltransferase, BMA, CGTase, neutral-cyclodextrin glycosyltransferase, or 1,4-α-D-glucan 4-α-D-(1,4-α-D-glucano)-transferase. Cyclomaltodextrin glucanotransferases are capable of catalyzing the hydrolysis and the formation of (1→4)-α-D-glucosidic bonds, and in particular the formation of cyclic maltodextrins from polysaccharides as well as the disproportionation of linear oligosaccharides.

Dextransucrase is an enzyme assigned with enzyme classification number EC 2.4.1.5, and is also known as sucrose 6-glucosyltransferase, SGE, CEP, sucrose-1,6-α-glucan glucosyltransferase or sucrose: 1,6-α-D-glucan 6-α-D-glucosyltransferase. Dextransucrases are capable of catalyzing the reaction: sucrose+[(1→6)-α-D-glucosyl]$_n$=D-fructose+[(1→6)-α-D-glucosyl]$_{n+1}$.

The enzyme may be dissolved in the reaction mixture or immobilized on a solid support which is contacted with the reaction mixture. If the enzyme is immobilised, it is attached to an inert carrier. Suitable carrier materials are known in the art. Examples for suitable carrier materials are clays, clay minerals such as kaolinite, diatomeceous earth, perlite, silica, alumina, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For preparing carrier-bound enzymes the carrier materials usually are used in the form of fine powders, wherein porous forms are preferred. The particle size of the carrier material usually does not exceed 5 mm, in particular 2 mm. Further, suitable carrier materials are calcium alginate and carrageenan. Enzymes may directly be linked by glutaraldehyde. A wide range of immobilisation methods is known in the art (e.g. J. Lalonde and A. Margolin "Immobilization of Enzymes" in K. Drauz und H. Waldmann, Enzyme Catalysis in Organic Synthesis 2002, Vol. III, 991-1032, Wiley-VCH, Weinheim).

The enzymatically catalyzed reaction can be carried out batch wise, semi-batch wise or continuously. Reactants can be supplied at the start of reaction or can be supplied subsequently, either semi-continuously or continuously. The catalytic amount of glycosidase or glycosyltransferase required for the method of the invention depends on the reaction conditions, such as temperature, solvents and amount of substrate.

The reaction can be performed in aqueous media such as buffer. A buffer adjusts the pH of the reaction mixture to a value suitable for effective enzymatic catalysis. Typically the pH is in the range of about pH 4 to about pH 9, for example of about pH 5 to about pH 7. Suitable buffers comprise, but are not limited to, sodium acetate, tris(hydroxymethyl)aminomethane ("Tris") and phosphate buffers.

Optionally, the reaction takes place in the presence of a solvent mixture of water and a water miscible organic solvent at a weight ratio of water to organic solvent of from 0.1:1 to 9:1, for example from 1:1 to 3:1. The organic solvent is no primary or secondary alcohol and, accordingly, is non-reactive towards the polysaccharide. Suitable organic solvents comprise alkanones, alkylnitriles, tertiary alcohols and cyclic ethers, and mixtures thereof, for example acetone, acetonitrile, t-pentanol, t-butanol, 1,4-dioxane and tetrahydrofuran, and mixtures thereof. Generally, the use of organic solvents is not preferred.

A "water miscible organic solvent" is understood to mean an organic solvent that forms a homogeneous mixture with water at the weight ratio of water to organic solvent used.

The concentration and the ratio of the reactants, i.e. polysaccharide and ethylenically unsaturated compound of formula II, may be adapted to the optimum reaction conditions. For example, the initial polysaccharide concentration may be in the range of 10 to 400 g/l, relative to the total volume of the reaction mixture, for example 50 g/l.

The reaction temperature may be adapted to the optimum reaction conditions, which may depend on the specific enzyme applied. The reaction may expediently take place at temperatures between the freezing point of the reaction mixture and the denaturation temperature of the enzyme. Upon reaching the denaturation temperature the catalytic activity of the enzyme is lost. For example, the reaction may be performed at a temperature in the range from 0° C. to 80° C., for example from 30° C. to 65° C. The process may proceed until equilibrium between reactants and products is achieved, but may be stopped earlier. Usual process times are in the range from 1 h to 96 h.

The methodology of the present invention can further comprise a step of recovering the produced ethylenically unsaturated glycoside of formula I. The term "recovering" includes extracting, harvesting, isolating or purifying the compound from the reaction mixture. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like Thin Layer Chromatography (TLC), High Performance Liquid Chromatography (HPLC), gas chromatography (GC), Spectroscopy (e.g. IR, UV, NMR spectroscopy), coloring methods, NIRS, or enzymatic assays.

The examples described below are intended to illustrate the present invention without limiting it in any way.

EXAMPLE 1

Cellulase Catalyzed Synthesis of
2-(β-glucosyloxy)-ethyl acrylate from Cellulose 0.5 g cellulose was suspended in 10 ml 50 mM sodium acetate buffer at pH 5.0 containing 1 ml 2-hydroxyethyl acrylate. The reaction was started by addition of 0.010 g (60 U) cellulase from *Trichoderma reesei*. The reaction mixture was stirred for 3 days at 37° C. The product was detected by thin layer chromatography (TLC) (chloroform/methanol 4/1 (v/v), Rf 0.55). Unreacted cellulose was removed by filtration and the product was purified by column chromatography (silica gel, eluant: chloroform/methanol 7/1 (v/v)). Fractions containing the aimed product were pooled and the solvent was removed by rotary evaporation. Yield: 9.4 mg (2% of total cellulose).

$^1$H-NMR δ in ppm: 3.2-4.2 GlucOCH$_2$CH$_2$R (8p); 4.38 GlucOCH$_2$CH$_2$R (2p Tri J 4.38 4.38 Hz); 4.50 GlucH$_1$ (1p Dou J 7.92 Hz); 5.99 H$_{trans}$CH=CHR (1p Dou J 10.42 Hz); 6.22 CH$_2$=CHR (1p DDou J 17.30 10.47 Hz); 6.46 H$_{cis}$CH=CHR (1p Dou J 17.31 Hz)

$^{13}$C-NMR δ in ppm: 60.9 GlucC$_6$; 64.4 OCH$_2$CH$_2$; 68.1 OCH$_2$CH$_2$; 69.8 GlucC$_5$; 73.3 GlucC$_2$; 75.9 GlucC$_3$; 76.1 GlucC$_4$; 102.7 GlucC$_{1β}$; 127.6 H$_2$C=CHR; 132.9 H$_2$C=CHR; 168.6 O(O)CR ESI-MS pos: calculated: 301.09 (C11H18O8Na); observed: 301.25

EXAMPLE 2

Amylase Catalyzed Synthesis of
2-(α-maltosyloxy)-ethyl acrylate from Starch 5.0 g soluble starch was suspended in 50 ml 50 mM sodium acetate buffer at pH 5.0 containing 50 ml 2-hydroxyethyl acrylate. The reaction was started by addition of 10 ml (32000 MANU) maltogenic amylase from *Bacillus stearothermophilus*. The reaction mixture was stirred for 4 days at 55° C. The product was detected by TLC (chloroform/methanol 2/1 (v/v), Rf 0.45). The remaining 2-hydroxyethyl acrylate was removed by extraction with diethyl ether. The aqueous layer was concentrated by rotary evaporation at 30° C. The unreacted starch was precipitated in isopropanol and removed by filtration. The filtrate was concentrated by rotary evaporation at 30° C. and the product was further purified by column chromatography (silica gel, eluant: chloroform/methanol 3/1 (v/v)). Fractions containing the aimed product were pooled and the solvent was removed by rotary evaporation.

Yield: 0.408 g (8%) Purity: >85

$^1$H-NMR δ in ppm: 3.2-4.2 Gluc$_{1-2}$OCH$_2$CH$_2$R (14p); 4.38-4.50 GlucOCH$_2$CH$_2$R (2p); 4.96 Gluc$_1$H$_1$ (1 p Dou J 3.75 Hz); 5.35 Gluc$_2$H$_1$ (1p Dou J 3.76 Hz); 5.99 H$_{trans}$CH=CHR (1p Dou J 10.43 Hz); 6.21 CH$_2$=CHR (1p DDou J 17.29 10.45 Hz); 6.44 H$_{cis}$CH=CHR (1p Dou J 17.30 Hz)

$^{13}$C-NMR δ in ppm: 60.6 Gluc$_2$C$_6$;63.5 Gluc$_1$C$_6$;64.1 OCH$_2$CH$_2$;67.7 OCH$_2$CH$_2$; 69.5 Gluc$_1$C$_5$;71.2 Gluc$_2$C$_5$; 72.0 Gluc$_1$C$_2$;72.9 Gluc$_1$C$_3$;73.1 Gluc$_2$C$_3$;73.6 Gluc$_2$C$_2$; 76.3 Gluc$_1$C$_4$;77.5 Gluc$_2$C$_4$;98.2 Gluc$_1$C$_{1\alpha}$;100.1 Gluc$_2$C$_{1\square}$; 127.7H$_2$C=CHR; 132.8H$_2$C=CHR; 168.0 O(O)CR ESI-MS pos: calculated: 463.1422 (C17H28O13Na); observed: 463.3333

EXAMPLE 3

Cyclodextrin Glycosyltransferase Catalyzed Synthesis of 2-(β-maltriosyloxy)-ethyl acrylate from Starch 0.634 g 2-(β-glucosyloxy)-ethyl acrylate and 1.0 g soluble starch were dissolved in 10 ml Tris-HCl buffer at pH 7.0 containing 0.01 M calcium chloride and 0.004 g MEHQ. The reaction was started by addition of 0.1 ml (60 U) cyclodextrin glycosyltransferase from *Bacillus macerans*. The reaction mixture was stirred for 1.5 h at 60° C. The product was detected by TLC (acetonitrile/water/ammonia 6/3/1 (v/v), Rf 0.27 and purified by column chromatography (silica gel, eluant: ethyl acetate/methanol 4/1 (v/v)). Fractions containing the aimed product were pooled and the solvent was removed by rotary evaporation. Product: α-D-glucopyranosyl-(1-4)-α-D-glucopyranosyl-(1-4)-β-glucopyranosyl-oxyethyl acrylate. Yield: 0.241 g (38 w %) Purity: 95%

$^1$H-NMR δ in ppm: 3.2-4.2 Gluc$_{1-3}$OCH$_2$CH$_2$R (20p); 4.39 GlucOCH$_2$CH$_2$R (2p Tri J 4.38 4.38 Hz); 4.50 Gluc$_1$H$_t$ (1p Dou J 7.91 Hz); 5.39 Gluc$_{2-3}$H$_t$ (2p Sin) 5.99 H$_{trans}$CH=CHR (1p Dou J 10.46 Hz); 6.22 CH$_2$=CHR (1p DDou J 17.29 10.46 Hz); 6.46 H$_{cis}$CH=CHR (1p Dou J 17.30 Hz)

$^{13}$C-NMR δ in ppm: 60.7 Gluc$_{2-3}$C$_6$; 60.8 Gluc$_1$C$_6$; 64.4 OCH$_2$CH$_2$; 68.1 OCH$_2$CH$_2$; 69.5 Gluc$_1$C$_5$; 71.4 Gluc$_2$C$_5$; 71.7 Gluc$_2$C$_5$; 72.0 Gluc$_2$C$_2$; 72.9 Gluc$_2$C$_3$; 73.1 Gluc$_{2-3}$C$_3$; 73.5 Gluc$_2$C$_2$; 74.8 Gluc$_2$C$_2$; 76.3 Gluc$_2$C$_4$; 77.0 Gluc$_2$C$_4$; 77.1 Gluc$_2$C$_4$; 99.7 Gluc$_3$C$_{1\alpha}$; 100.0 Gluc$_2$C$_{1\alpha}$; 102.5 Gluc$_1$C$_{1\beta}$; 127.6H$_2$C=CHR; 132.9H$_2$C=CHR; 168.7 O(O)CR ESI-MS pos: calculated: 625.1950 (C23H38O18Na); observed: 625.1957

The invention claimed is:

1. A method for producing an ethylenically unsaturated glycoside of formula I

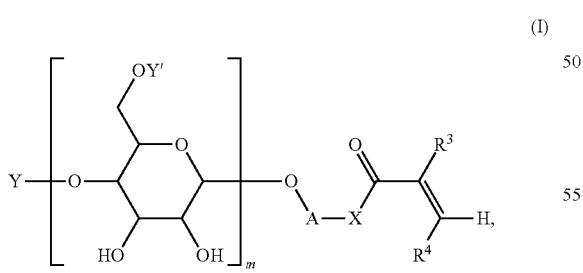

wherein
Y and Y' are independently H, or a monosaccharide or a linear or branched oligosaccharide comprising from 2 to 12 monosaccharide units, wherein at least one of Y and Y' is other than H;
m is an integer of from 0 to 3;
A is C$_{2-20}$ alkylene or —R$^6$—O—[—R$^6$—O—]$_x$—C$_{2-20}$ alkylene;
X is selected from the group consisting of —O—, —NH— and —NR$^5$—,
R$^3$ is selected from the group consisting of —H, and C$_{1-10}$ alkyl;
R$^4$ is selected from the group consisting of —H, —COOH and —COO$^-$ M$^+$;
R$^5$ is C$_{1-10}$ alkyl;
R$^6$ is —C$_2$H$_4$— or —C$_3$H$_6$—;
M$^+$ is selected from the group consisting of Li$^+$, Na$^+$, K$^+$ and NH$_4^+$; and
x is an integer of from 0 to 200;
comprising reacting an ethylenically unsaturated compound of formula II

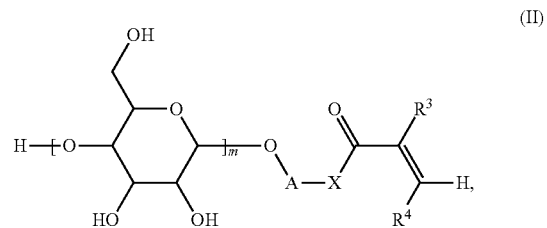

with a polysaccharide comprising 10 or more monosaccharide units in the presence of a glycosidase or a glycosyltransferase.

2. The method of claim 1, wherein the polysaccharide is a compound of formula III:

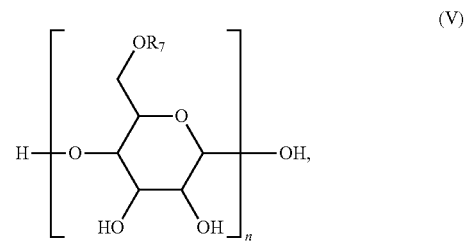

wherein R$^7$ is —H or a radical of formula VI:

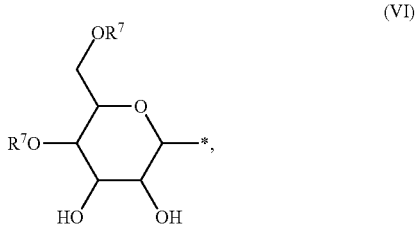

wherein in peripheral monosaccharide units R$^7$ is H and n is such that the number of monosaccharide units encompassed by the recurring units in brackets is 10 or more.

3. The method of claim 1, wherein Y' is H.

4. The method of claim 1, wherein
A is C$_{2-6}$ alkylene;
X is —O—; and
R$^3$ is —H, or —CH$_3$.

5. The method of claim 1, wherein
m is 1; and
Y is selected from the group consisting of monosaccharides, disaccharides and trisaccharides.

6. The method of claim 1, wherein the glycosidase is selected from the group consisting of amylases, cellulases, glucosidases and galactosidases.

7. The method of claim 1, wherein the glycosyltransferase is selected from the group consisting of cyclomaltodextrin glucanotransferases.

8. The method of claim 1, wherein the polysaccharide is selected from the group consisting of starch, amylose, amylopectin, cellulose, and mixtures thereof.

* * * * *